United States Patent
Murali et al.

(10) Patent No.: US 11,419,650 B2
(45) Date of Patent: Aug. 23, 2022

(54) SYSTEM AND METHOD FOR TRACKING TORSION OF A SCREW

(71) Applicant: OrthoScrews, LLC, Dothan, AL (US)

(72) Inventors: Sudarsan Murali, Tuscaloosa, AL (US); Zoe E Guckien, Tuscaloosa, AL (US); Alec Hopkirk, Tuscaloosa, AL (US)

(73) Assignee: OrthoScrews, LLC, Dothan, AL (US)

( * ) Notice: Subject to any disclaimer, the term of this patent is extended or adjusted under 35 U.S.C. 154(b) by 389 days.

(21) Appl. No.: 16/743,984

(22) Filed: Jan. 15, 2020

(65) Prior Publication Data
US 2020/0222092 A1 Jul. 16, 2020

Related U.S. Application Data

(60) Provisional application No. 62/793,009, filed on Jan. 16, 2019.

(51) Int. Cl.
| | |
|---|---|
| *A61B 17/80* | (2006.01) |
| *A61B 34/20* | (2016.01) |
| *G16H 40/40* | (2018.01) |
| *G16H 40/67* | (2018.01) |
| *A61B 17/86* | (2006.01) |
| *A61B 90/00* | (2016.01) |

(52) U.S. Cl.
CPC ........ *A61B 17/808* (2013.01); *A61B 17/8038* (2013.01); *A61B 17/8695* (2013.01); *A61B 34/20* (2016.02); *A61B 90/06* (2016.02); *G16H 40/40* (2018.01); *G16H 40/67* (2018.01); *A61B 2034/2046* (2016.02); *A61B 2090/066* (2016.02)

(58) Field of Classification Search
CPC ............ A61B 17/8038; A61B 17/8695; A61B 17/808; A61B 17/8625; A61B 17/8605; A61B 2562/0247; A61B 2562/0257; A61B 2562/0252; A61B 2090/064; A61B 2090/065; A61B 2090/066; G01L 5/0004; G01L 5/0057
See application file for complete search history.

(56) References Cited

U.S. PATENT DOCUMENTS

2020/0022772 A1* 1/2020 Benson ................. G01L 5/0004

* cited by examiner

*Primary Examiner* — Samuel S Hanna
(74) *Attorney, Agent, or Firm* — AdamsIP, LLC

(57) ABSTRACT

A system for determining the torsion of a screw is provided. The system generally comprises a first washer, second washer, spring, radio frequency identification (RFID) tag, and interrogation device. A screw is inserted through the system and provides the compression force necessary to bring the first washer and second washer separated by the spring in contact with one another, thus creating a complete circuit from the first circuit portion and second circuit portion of the signal transmitter. The interrogation device is used to send and receive information to and from the signal transmitter. An encasing may be used to encapsulate the first washer, second washer, spring, and signal transmitter in a way such that they are protected from the environment.

15 Claims, 4 Drawing Sheets

SYSTEM AND METHOD FOR TRACKING TORSION OF A SCREW

CROSS REFERENCES TO RELATED APPLICATIONS

This application claims priority to U.S. Provisional Patent Application Ser. No. 62/793,009, filed Jan. 16, 2019, in which said application is incorporated herein in its entirety by reference.

FIELD OF THE DISCLOSURE

The subject matter of the present disclosure refers generally to a system that relays torsion data of a screw.

BACKGROUND

Broken bones and strained or torn ligaments and tendons must be carefully stabilized and supported until they are strong enough to handle the body's weight and/or movement. It is known that bone heals better if the fracture fragments are pressed firmly together due to an increased contact area across the fracture as well as increased stability of the fracture while decreasing the fracture gap. Modern surgical procedures have allowed physicians to internally set and stabilize fractured bones and support damaged tendons and ligaments, which has greatly increased the effectiveness of orthopedic treatments. The use of surgical implants to hold bones together, strengthen tendons and ligaments, or attach tendons and ligaments to bone is the standard of care in orthopedic medicine. For instance, high ankle sprains can now be treated more effectively via a surgical procedure using implants to hold the bones, tendons, and ligaments of the ankle in closer relation to one another than using more traditional non-invasive methods such as rest.

Two of the main surgical implants used by physicians are washers and screws. Screws are used for internal fixation more often than any other type of implant. Screws are easily adaptable to a specific injury by altering aspects of the screw such as thread slope and thread length, making them highly adaptable to the procedures in which they will be used. This is especially useful since bones vary greatly in size, shape, and strength. Screws can be used alone to hold a fracture or may be used in conjunction with plates, rods, washers, or nails. Washers are generally used with screws to distribute the stresses under the screw head to surrounding bone and tissue as to not put too much pressure in a small area, thus reducing the potential for further injury. For instance, a washer may be used with a screw to prevent thin cortical bone from splitting by increasing the area in which pressure is applied by the screw head. Washers can also be used to fasten ligaments separated from bone, avulsion fractures, and comminuted fractures. For instance, a washer having teeth may be used in conjunction with a screw to grip tendons or ligaments that have separated from bone and hold them in place.

After the bone heals, screws and washers may be either left in place or removed. In instances where the screws and washers are left in place, orthopedic screws may loosen over time despite being designed to have a tight hold on bone due to improper insertion, excess force, or other factors such as decreased bone integrity or infection. As the screws loosen, a patient may experience tissue, muscle, and/or nerve damage. A patient may also see performance issues when participating in physical activities as biomechanics may be altered due to deteriorating function of the surgical implants holding bones and ligaments in place. Optimal torsion is presently achieved utilizing a torque sensitive screwdriver, but it can be difficult to determine when a procedure must be performed to tighten or replace a potentially compromised surgical implant. Surgical screws are currently monitored using Computed Tomography (CT) and/or X-Ray imaging, which can be inaccurate in detecting minute loosening, subject to artifact, costly, and increase patient exposure to radiation. Further complicating the matter is that surgical implants made of plastic do not show up on an X-ray, which only makes it even more difficult to determine if a surgical implant of a patient has loosened.

Accordingly, there is a need in the art for a system that may relay information regarding any changes in torsion a screw may experience after implantation.

DESCRIPTION

A system for determining the torsion of a screw is provided. In one aspect, the system protects patients from suffering damage caused by loosened orthopedic screws. In another aspect, the system estimates whether the orthopedic screw is under a proper amount of torque. Generally, the system of the present disclosure is designed to determine whether a screw has loosened over time. The system generally comprises a first washer, a second washer, a spring, a signal transmitter, and an interrogation device. A screw is inserted through the system and provides the compression force necessary to bring the first washer and second washer in contact with one another, creating a complete circuit from the first circuit portion and second circuit portion. In one preferred embodiment, the RFID may be interrogated using an external interrogation device in such a way that the RFID may transmit and/or receive radio signals using an external power supply. In another preferred embodiment, an encasing may be used to encapsulate the first washer, second washer, spring, and signal transmitter in a way such that they are protected by the environment within a patient.

A screw comprises a trailing end, advancing end, and proximal portion having plurality of threads that convert a rotational force into a compression force. The head of the orthopedic screw generally has a larger radius than the proximal portion and is located at the trailing end. Rotational force applied to a head of the orthopedic screw may cause the plurality of threads to engage the entity in which the orthopedic screw is being secured. The plurality of threads of the proximal portion may vary in form, angle, depth, and pitch, depending on the need. A washer may comprise an upper end, lower end, outer surface, and inner surface that defines a central bore. The screw may be inserted into the washer via the bore. As the screw is inserted through the bore and into the entity, the head of the screw may come into contact with the surface of the washer at the upper end. The diameter of the bore at the upper end of the washer is preferably smaller than the diameter of the trailing end of the particular screw paired with the washer. The washer preferably has a width along its longitudinal axis such that any pressure applied to the washer by the trailing end of the screw will not cause the trailing end of the screw to pass through the washer.

The upper surface and/or lower surface of the washer may further comprise a signal transmitter. In a preferred embodiment, the signal transmitter may comprise a first circuit portion, second circuit portion, and microchip. The first circuit portion and second circuit portion may be attached to a first washer and second washer. In a preferred embodiment, the first circuit portion and second circuit portion may be arranged on the first washer and second washer in a way such that a complete circuit is created when the first washer and second washer are within a certain minimal distance from one another. In a preferred embodiment, the completed circuit creates an antenna for a signal transmitter. A spring may be used to separate the first washer and the second washer. As the spring is compressed between the first washer and second washer of the system, the first circuit portion and second circuit portion may come in closer relation with one another until a completed circuit is formed. The spring is preferably of a diameter such that it is just wider than the bore. The elastic potential energy of the spring is preferably large enough to push the first washer and second washer away from one another when a sufficient compression force is not applied. The screw preferably provides the compression force necessary to complete the circuit.

The microprocessor may receive instructions from an interrogation device via the complete circuit and perform an action based on those instructions. For instance, an interrogation device may transmit instructions to the microprocessor of the microchip via the complete circuit that cause the microprocessor to retrieve data from the memory of the signal transmitter and transmit said data to the interrogation device via the complete circuit. Memory of the signal transmitter stores information that may be transmitted to an interrogation device. In some preferred embodiments, memory may include one or more volatile memory units. In another preferred embodiment, memory may include one or more non-volatile memory units. The completed circuit is operably connected to the microchip in a way such that it may transmit information received via radio waves from the interrogation device to the microchip. The completed circuit may also receive electromagnetic energy from the interrogation device and convert that energy into electricity that may be used to power the microchip. The shape of the completed circuit may differ depending on the frequency at which the signal transmitter is to operate. The first circuit portion and second circuit portion are deposited or printed on the first washer and second washer such that when they are brought into contact with one another a completed circuit is formed. The microchip may then be attached to one of the first circuit portion or second circuit portion such that it may receive data and/or energy from a completed circuit.

The foregoing summary has outlined some features of the system of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and process disclosed herein. Those skilled in the pertinent art should also realize that such equivalent designs or modifications do not depart from the scope of the process of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including process steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally. Where reference is made herein to a process comprising two or more defined steps, the defined steps can be carried out in any order or simultaneously (except where the context excludes that possibility), and the process can include one or more other steps which are carried out before any of the defined steps, between two of the defined steps, or after all the defined steps (except where the context excludes that possibility).

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components. As used herein, the term "screw" and grammatical equivalents thereof refers to screws, dowels, bolts, and rivets. As used herein, the term "washer" and grammatical equivalents thereof refers to washers and nuts. As used herein, the term "patient" or grammatical equivalents thereof refers to humans and animals.

Figure 1:
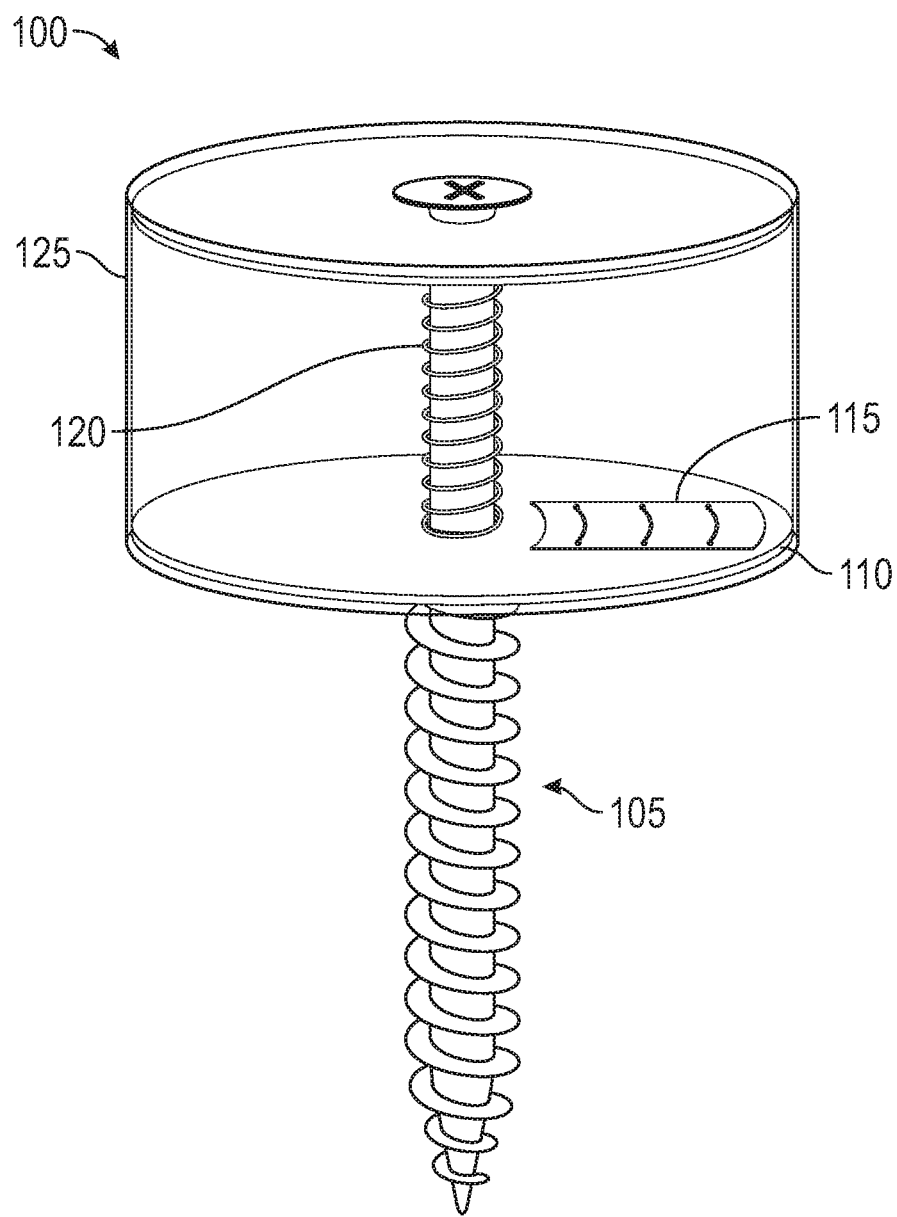
FIG. 1 is a perspective view of a system in which techniques described herein may be implemented.
Figure 2:
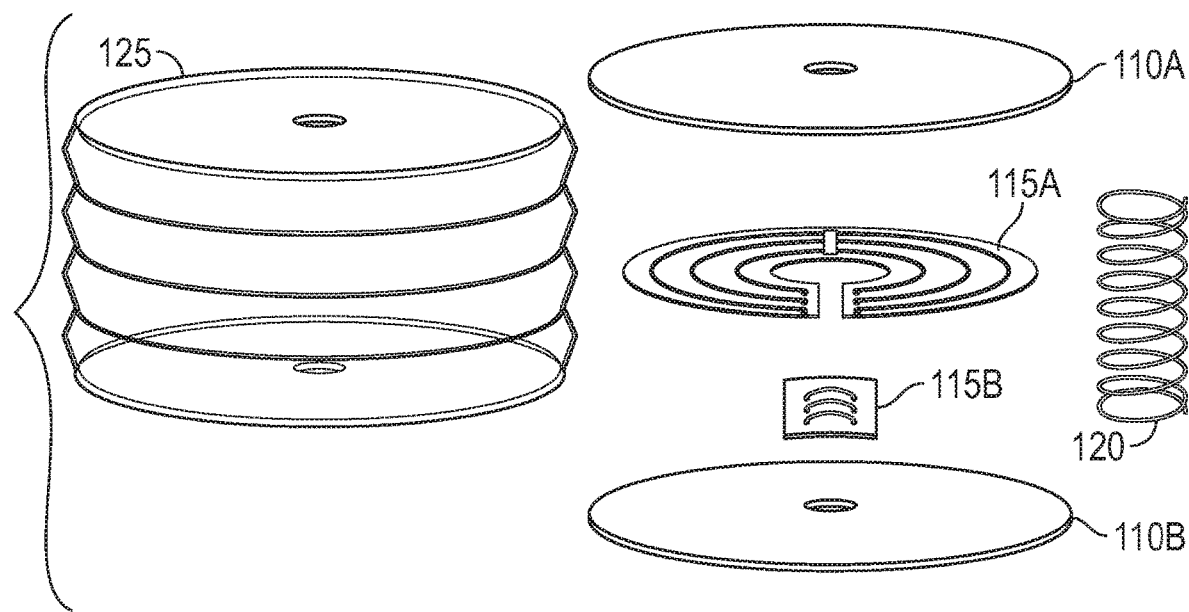
FIG. 2 is an exploded view of a system in which techniques described herein may be implemented.

FIGS. 1-6 illustrate embodiments of a system 100 and its various methods for determining the torsion of a screw 105. As illustrated in FIGS. 1 and 2, the system 100 generally comprises a torsion tracking device comprising a first washer 110A, a second washer 110B, a spring 120, and a signal transmitter 115 and a screw 105 inserted through the torsion tracking device that provides the compression force necessary to bring the first washer 110A and second washer 110B in contact with one another, which in turn brings the first circuit portion 115A and second circuit portion 115B of the signal transmitter 115 in contact with one another to form a completed circuit. In some preferred embodiments, the system 100 may further comprise a screw preinserted through the torsion tracking device in a way such that the screw 105 may not be removed, as is illustrated in FIG. 1. An interrogation device 510 may be used to read the signals of the system. In a preferred embodiment, the interrogation device is a RFID reader that may read radio frequency (RF) signals produced by the signal transmitter 115. In another preferred embodiment, the signal transmitter 115 is an RFID tag. In a preferred embodiment, the signal transmitter 115 may be operably connected to a power supply in a way such that the signal transmitter 115 may transmit and/or receive RF signals using said power supply as a power source. In another preferred embodiment, an encasing 125 may be used to encapsulate the first washer 110A, second washer 110B, spring 120, and signal transmitter 115 in a way such that they are protected from the environment within a patient 505.

Figure 3:
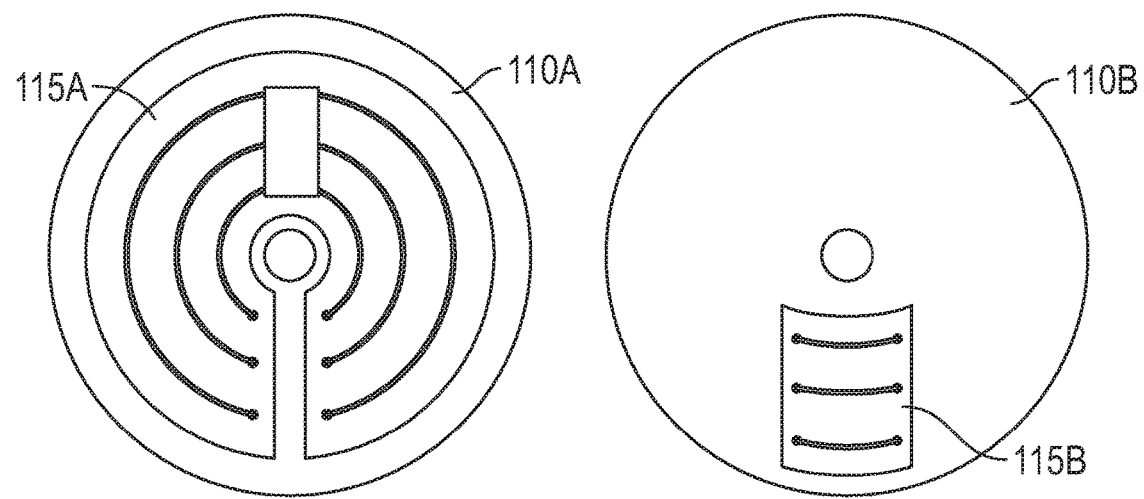
FIG. 3 is a perspective view of a first washer and second washer having a first circuit portion and second circuit portion attached thereon.
Figure 4:
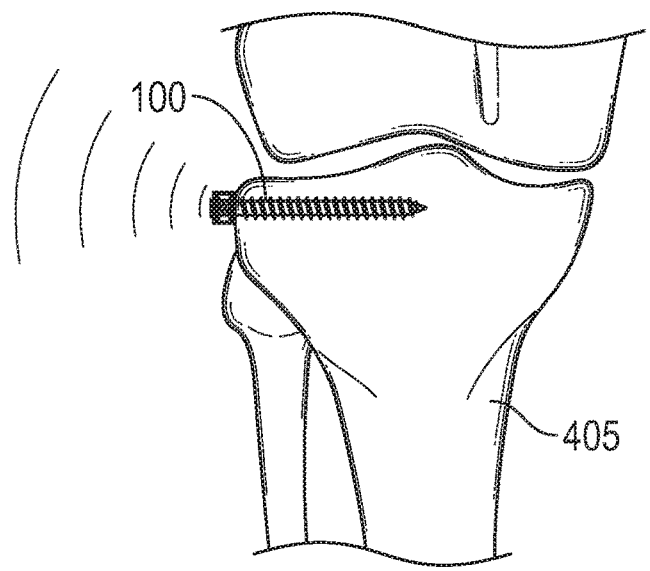
FIG. 4 is a depiction of an environment in which the system may be implemented.
Figure 5:
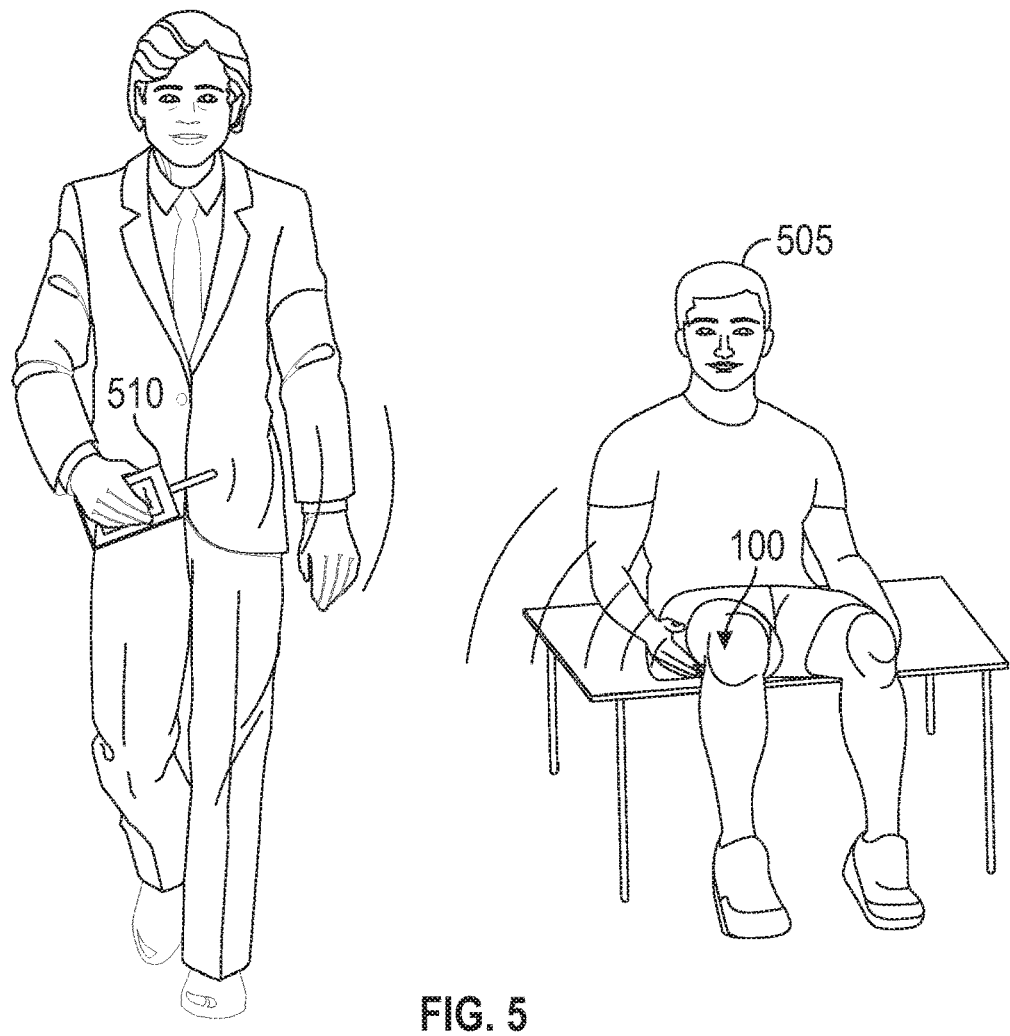
FIG. 5 is a depiction of how a physician may use an interrogation device to obtain information from the system when implanted within a patient.
Figure 6:
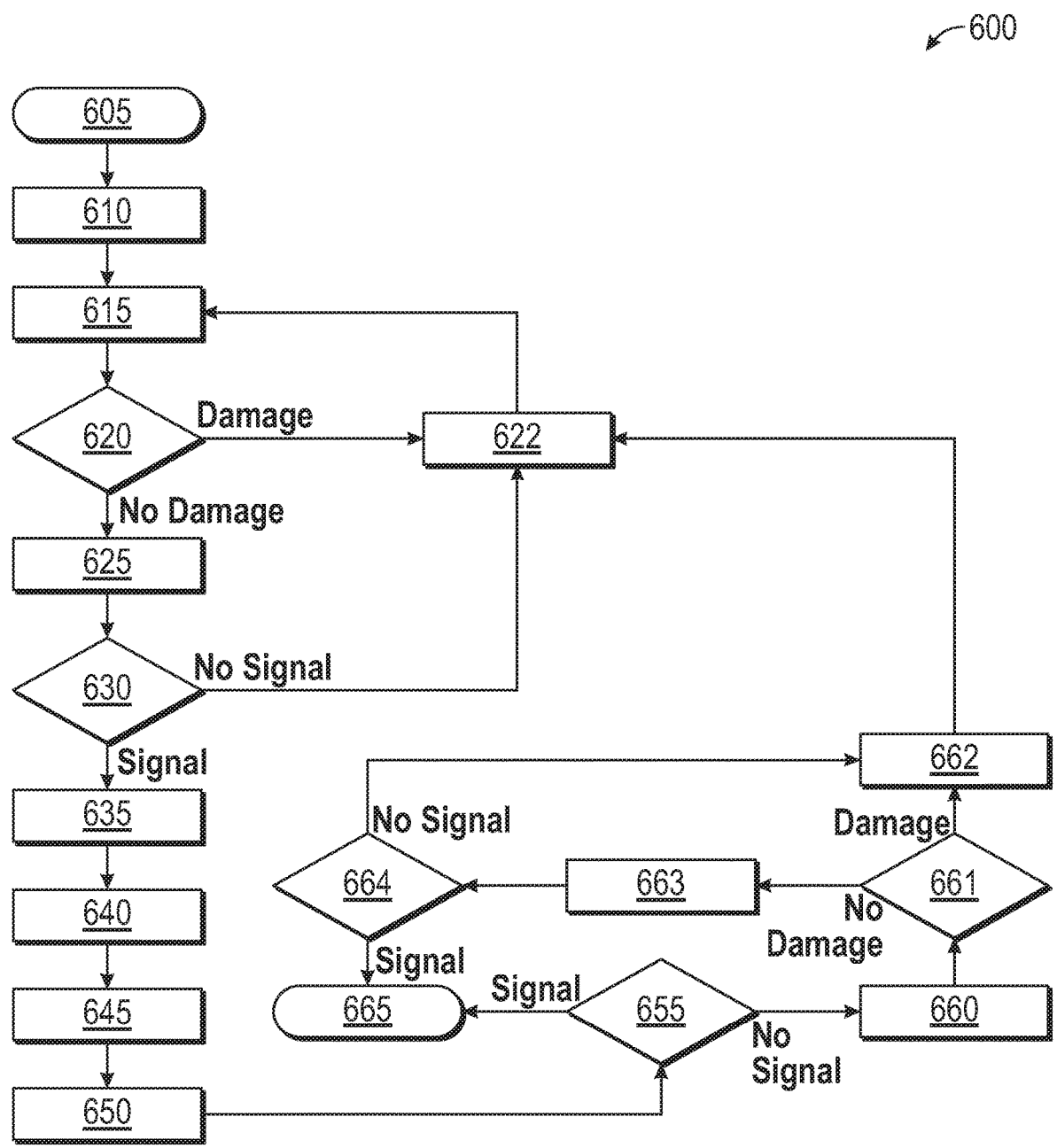
FIG. 6 is a flow chart diagramming how a physician may use the system as a surgical implant during an orthopedic procedure.

Although the system 100 and method of the present disclosure will primarily be discussed for use within the orthopedic surgery field, one of skill in the art will appreciate that the inventive subject matter disclosed herein may be utilized in other fields or for other applications in which a screw 105 that relays torsion data is needed. It is understood that the various method steps associated with the methods of the present disclosure may be carried out as operations by the system 100 shown in FIG. 1. FIG. 2 illustrates an exploded view of a screw 105 that may relay torsion data. FIG. 3 illustrates the various components of a signal transmitter 115 that may be used to transmit torsion data to an interrogation device 510. FIG. 4 illustrates how the first circuit portion 115A and second circuit portion 115B of the signal transmitter 115 work together to generate torsion data. FIG. 5 illustrates how a physician may use the system 100 and an interrogation device 510 to determine whether an orthopedic screw is of an appropriate tightness within a patient 505. FIG. 6 illustrates a method that may be carried out by a physician when using the system 100 as an implant device in an orthopedic procedure.

A screw 105 may be defined as a cylindrical body used for securing at least two objects to one another, wherein said cylindrical body comprises a trailing end, advancing end, and proximal portion having plurality of threads that convert a rotational force into a compression force. Types of screws 105 that may be used in the system 100 include, but are not limited to, orthopedic screws, wood screws, concrete screws, masonry screws, drive screws, decking screws, socket cap screws, dowels, eye bolts, lag bolts, carriage bolts, hex bolts, shoulder bolts, square head bolts, POP rivets, multi-grip rivets, and structural rivets, or any combination thereof. An orthopedic screw may be defined as a screw 105 used for medical purposes. As illustrated in FIG. 1, the head of an orthopedic screw generally has a larger radius than the proximal portion and is located at the trailing end. In one preferred embodiment, the head of the screw 105 is not cylindrical in shape. For instance, the head of the screw 105 may be rectangular or octahedral in shape. The head of the screw 105 may have a centrally located indentation on its upper surface that may fit a tool, wherein the tool may apply a rotational force. The rotational force applied to the head of the screw 105 may cause the plurality of threads of the proximal portion to engage the entity 405 in which the screw 105 is being secured.

In a preferred embodiment, as illustrated in FIG. 4, the entity 405 in which the screw 105 is being secured is bone. The proximal portion of the screw 105 may have a fixed diameter or it may have a varied diameter. For instance, the diameter of the proximal portion having a plurality of threads may be larger than the diameter of the proximal portion not having a plurality of threads. In one preferred embodiment, the proximal portion may end in a tip, wherein the proximal portion is threaded all the way to the tip. This may allow a user to implant a screw 105 without the need of predrilling a hole into the entity 405 in which the screw 105 is to be placed. The plurality of threads of the proximal portion may vary in form, angle, depth, and pitch, depending on the need. For instance, the shape of the plurality of threads of an orthopedic screw designed for cortical bones may have a smaller pitch, which may result in more threads along the proximal portion. For instance, the shape of the plurality of threads of an orthopedic screw designed for cancellous bones may be deeper since cancellous bones are more fragile. This may provide an orthopedic screw designed for cancellous bone more grip and prevent stripping or loosening.

A washer 110 may be defined as a conical body having a central bore extending longitudinally through the washer 110 and defined by an inner surface, wherein the diameter of the central bore is no wider than the head on the trailing end of the screw 105 in which the washer 110 is paired. In some preferred embodiments of a washer 110, the central bore may have a plurality of threads that fit the plurality of threads of the screw 105 in which the washer 110 is paired. Types of washers that may be used within the system include, but are not limited to, dock washers, fender washers, finishing cup washers, flat washers, split ring lock washers, tooth lock washers, NAS washers, neoprene EPDM washers, structural washers, square washers, cap nuts, castle nuts, coupling nuts, flange serrated nuts, hex finish nuts, hex jam nuts, hex machine nuts, keps nuts, thumb nuts, nylon insert lock nuts, square nuts, tee nuts, shear nuts, tri-groove nuts, and wing nuts, or any combination thereof. A washer 110 comprises an upper end, a lower end, an outer surface, and an inner surface. The screw 105 may be inserted into a washer 110 via the bore. As the screw 105 is inserted into the entity 405, the head of the screw 105 may come into contact with the surface of the washer 110 at the upper end. The larger surface area of the washer 110 may spread the compression force of the screw 105 over a larger area of the entity 405, thus decreasing the likelihood that too much pressure is applied to a portion of the entity 405 in which the screw 105 is being implanted.

The diameter of the bore at the upper end of the washer 110 is preferably smaller than the diameter of the trailing end of the particular screw 105 paired with the washer 110. In some embodiments of a washer 110, the interior surface may be tapered such that the central bore's diameter is largest at the upper end. In embodiments such as this, the bore at the upper end may be larger than the width of the trailing end of the screw 105; however, the width of the bore at the lower end of the washer 110 may be smaller than the width of the trailing end of the screw 105. The washer 110 preferably has a width along its longitudinal axis such that any pressure applied to the washer 110 by the trailing end of the screw 105 will not cause the trailing end of the screw 105 to pass through the washer 110. In another preferred embodiment, the length of the washer 110 along its horizontal axis is long enough to countersink the head of the screw 105. In yet another preferred embodiment, the surface of the lower end of the washer 110 may comprise a plurality of teeth, wherein the plurality of teeth may grip material as the washer 110 makes forcible contact with the surface of the entity 405 via the screw 105, thus holding the material between the washer 110 and the surface of the entity 405.

As illustrated in FIGS. 1 and 3, the upper surface and/or lower surface of the washer 110 may further comprise a signal transmitter 115. In a preferred embodiment, the signal transmitter 115 may comprise a first circuit portion 115A, a second circuit portion 115B, and a microchip. The first circuit portion 115A and second circuit portion 115B may be attached to a first washer 110A and a second washer 110B. In a preferred embodiment, the first circuit portion 115A and second circuit portion 115B may be arranged on the first washer 110A and the second washer 110B in a way such that a complete circuit is created when said first washer 110A and said second washer 110B are within a certain distance from one another, thus placing the first circuit portion 115A and second circuit portion 115B in contact with one another. In yet another preferred embodiment, the first washer 110A and second washer 110B must be aligned in a way such that the first circuit portion 115A and second circuit portion 115B overlap in a way that creates the completed circuit. The completed circuit preferably creates an antenna for a signal transmitter 115; however, one with skill in the art will understand that other circuits may be formed by the coming together of the first circuit portion 115A and second circuit portion 115B. A compression force must be applied to the system 100 in order to form the complete circuit. In the preferred embodiment as illustrated in FIG. 4, the screw 105 may provide the compression force necessary to complete the circuit, wherein the head of the screw 105 may transfer compression energy to a washer 110, which in turn transfers the compression energy to a spring 120, thus compressing the spring 120 and allowing the first washer 110A and second washer 110B to make contact with one another.

In the preferred embodiment, as illustrated in FIGS. 1 and 2, a spring 120 may be used to separate the first washer 110A and the second washer 110B. As the spring 120 is compressed between the first washer 110A and second washer 110B of the system 100, the first circuit portion 115A and second circuit portion 115B may come in closer relation with one another. If the first circuit portion 115A and second circuit portion 115B are too far from one another to form a complete circuit, the signal transmitter 115 may not receive, transmit, or backscatter radio frequency waves to or from an interrogation device 510. If the first circuit portion 115A and second circuit portion 115B are not too far from one another to form a complete circuit, the signal transmitter 115 may then receive, transmit, or backscatter RF waves to/from and interrogation device 510. The spring 120 is preferably of a diameter such that it is just wider than the bore. However, one with skill in the art may recognize that the spring 120 may be of any width that may allow a screw 105 to penetrate the bore of the first washer 110A and second washer 110B while simultaneously applying a force that pushes the first washer 110A and second washer 110B away from one another. Preferably, the spring 120 encases the shaft of the screw 105 when the screw 105 is inserted through the bore of the first washer 110A and second washer 110B. The elastic potential energy of the spring 120 is preferably large enough to push the first washer 110A and second washer 110B away from one another when a sufficient compression force is not applied. In yet another preferred embodiment, more than one spring 120 may be used to separate the first washer 110A and second washer 110B The microchip of the signal transmitter 115 comprises a microprocessor, antenna, and memory. The microprocessor may be defined as a multipurpose, clock driven, register based, digital-integrated circuit which accepts binary data as input, processes it according to instructions stored in its memory, and provides results as output. The microprocessor may receive said instructions from an interrogation device 510 via the complete circuit forming an antenna and perform an action based on those instructions. For instance, an interrogation device 510 may transmit instructions to the microprocessor of the microchip via the complete circuit that cause the microprocessor to retrieve data from the memory and transmit said data to the interrogation device 510 via the complete circuit. Memory may be defined as a device capable of storing information permanently or temporarily. In the preferred embodiment, memory of the signal transmitter 115 stores information pertaining to a screw 105. This data may include, but is not limited to, date of implantation, torque amount, material composition of screw, thread slope, etc. In some preferred embodiments, memory may include one or more volatile memory units. In another preferred embodiment, memory may include one or more non-volatile memory units. A memory device may refer to storage space within a single storage device or spread across multiple storage devices. Types of devices that may act as memory may include, but are not limited to, read only memory (ROM), random access memory (RAM), and flash memory. ROM may comprise a conventional ROM device or another type of static storage device that stores static information and instructions for execution by the microprocessor. RAM may comprise a conventional RAM device or another type of dynamic storage device that stores information and instructions for execution by the processor.

As illustrated in FIGS. 4 and 5, the completed circuit is operably connected to the microchip in a way such that it may transmit information received via RF waves from the interrogation device 510 to the microchip. The completed circuit may also be used by the microchip to transmit/reflect the received signal back to the interrogation device 510. In one preferred embodiment, the completed circuit may receive electromagnetic energy from the interrogation device 510 and convert that energy into electricity that may be used to power the microchip. In a preferred embodiment, the completed circuit reflects signals from the reader in instances a power supply is not directly coupled to the microchip and transmits signals to the reader in instances a power supply is directly coupled to the microchip. The shape of the completed circuit may differ depending on the frequency at which the signal transmitter 115 is to operate. Shapes in which the completed circuit may be formed include, but are not limited to, spiral coil, single dipole, dual dipoles, and folded dipole, or any combination thereof. The first circuit portion 115A and second circuit portion 115B preferably comprise copper, aluminum, or silver. However, one with skill in the art will appreciate that the first circuit portion 115A and second circuit portion 115B may comprise of any material that may allow it to transmit and receive RF waves.

In a preferred embodiment, the first circuit portion 115A and second circuit portion 115B are deposited or printed on the first washer 110A and second washer 110B such that when they are brought into contact with one another a completed circuit is formed. The microchip may then be attached to one of the first circuit portion 115A or second circuit portion 115B such that it may receive data and/or energy from a completed circuit. In some embodiments, the first circuit portion 115A and second circuit portion 115B may be configured on a substrate deposited on the first washer 110A and/or second washer 110B. The substrate material is preferably able to withstand various environmental conditions the signal transmitter 115 may experience within the human body. Therefore, the substrate material is preferably made of a substance that may withstand salinity levels similar to those within the human body. The substrate material also preferably helps dissipate static buildup, provides a smooth printing surface, and is durable enough to withstand biomechanical action, as well as provide mechanical protection for the completed circuit and microchip. Some of the environmental conditions that may affect the substrate are heat, moisture, vibration, salts, abrasion, impact, and corrosion. In another preferred embodiment of the system 100, the first washer 110A, second washer 110B, spring 120, and signal transmitter 115 may be encapsulated by an encasing 125. The encasing 125 preferably comprises a material that allows penetration of RF waves. The encasing 125 also preferably comprises of a material that may withstand various environmental conditions experienced within the human body. Some of the environmental conditions that may affect the encasing 125 are heat, moisture, vibration, salts, abrasion, impact, and corrosion.

An interrogation device 510 may be defined as a device that transmits radio signals to a signal transmitter 115 and receives data from said signal transmitter 115. In some embodiments, the interrogation device 510 may also supply the signal transmitter 115 with power via electromagnetic waves. An interrogation device 510 generally comprises an antenna, high frequency interface, and a control section. The control section performs digital signal processing and procedures on data received from the signal transmitter 115. The control section also allows for wireless communication with signal transmitters via modulation, anti-collision procedures, and decoding transmissions received from said signal transmitter 115. The control section generally comprises a microprocessor, memory, and converters, wherein converters are used to convert analog signals into digital signals that may be transmitted via the antenna. The high frequency (HF) interface is used by the interrogation device 510 to transmit and receive RF signals. The HF interface generally comprises an oscillator, power amplifier, directional coupler low noise amplifier, and demodulator. The oscillator creates the RF signal, which is then modified to a particular frequency via the modulator.

Once the signal has been modulated by the modulator, the power amplifier then amplifies the modulated signal and sends it to the directional coupler that is operably connected to the antenna. The modulated signal is then transmitted via the antenna. When a signal transmitter 115 moves into the antenna's radio field, it becomes active and sends back to the antenna whatever information has been programmed into its memory via a backscattered or transmitted signal. The reader may then receive the signal transmitter's 115 backscattered/transmitted RF signal via the antenna. This received backscattered/transmitted RF signal may then be decoupled from any transmitted modulated RF signal by the directional coupler, and the low noise amplifier may amplify the received backscattered/transmitted signal before sending it to the demodulator, wherein the received backscattered/transmitted signal may be transformed into a demodulated signal. Once the received backscattered/transmitted RF signal has been demodulated, the demodulated signal may be transmitted to the control section, which may then perform an action based on the data contained in the demodulated signal.

FIG. 6 provides a flow chart 600 illustrating certain, preferred method steps that may be used to carry out the process of installing the system 110 within a patient 505. Step 605 indicates the beginning of the method. During step 610, the physician is to remove the system 100 from a sterile package. Once removed, the physician may inspect the system 100 during step 615. Depending on the results of the inspection, the physician may perform an action during step 620. If the physician determines that the system 100 appears damaged, the physician may obtain a new system 100 during step 622. The physician may then proceed to check the new system 100 during step 615. If the physician determines that the system 100 does not appear damaged, the physician may proceed to step 625. During step 625, the physician may manually compress the system 100 to determine if an RF signal is emitted by the system 100. Depending on the results of step 625, the physician may perform an action during step 630. If the physician determines no RF signal is emitted by the system 100 after compression, the physician may obtain a new system 100 during step 622. If the physician determines a RF signal is emitted by the system 100 after compression, the physician may proceed to step 635.

During step 635, the physician may slide the system 100 onto the orthopedic screw. Once the system 100 has been slid onto the orthopedic screw, the physician may implant the orthopedic screw into the entity 405 during step 640. After implantation, the physician may wash the system 100 with a saline solution during step 645. Once the system 100 has been washed, the physician may use an interrogation device 510 during step 650 to determine if the system 100 is emitting an RF signal. Based on the results of the step 650, the physician may perform an action during step 655. If the physician determines that the system 100 is emitting an RFID signal, the physician may proceed to the terminate method step 665. If the physician determines that the system 100 is not emitting an RF signal, the physician may proceed to step 660 and check for damage. Based on the results of this inspection, the physician may perform an action during step 661. If there is a physical defect visible, the physician may remove the system 100 during step 662 and proceed to step 622. If there is not a physical defect present, the physician may proceed to step 663 and incrementally tighten the orthopedic screw to determine if the orthopedic screw simply was not tightened enough. Based on the results of the tightening, the physician may perform an action during step 664. If the physician determines that an RF signal is not emitted by the system 100 despite the tightening of the orthopedic screw, the physician may proceed to step 662. If the physician determines that an RF signal has resulted from the tightening of the orthopedic screw, the physician may proceed to the terminate method step 665.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, materials, and arrangements of the parts and process stages which have been described and illustrated in order to explain the nature of this inventive subject matter can be made without departing from the principles and scope of the inventive subject matter.

What is claimed is:

1. A method for implanting a torsion tracking device in a patient comprising steps of:
    providing a torsion tracking device and a screw,
        wherein said torsion tracking device comprises an axially compressible encasing that surrounds a first distal plate, a second proximal plate, a spring, and at least two circuit portions,
        wherein said at least two circuit portions are attached to said first distal plate and said second proximal plate, wherein a shaft of said screw is positioned axially through said spring when said torsion tracking device is placed around said screw, wherein said spring provides an opposing axial force between said first distal plate and said second proximal plate, wherein said spring is configured to bias said first distal plate axially away from said second proximal plate, placing said torsion tracking device around said shaft of said screw and distal to a head of said screw, implanting said torsion tracking device and said screw into a bone of said patient, tightening said screw into said bone to a desired torque such that said torsion tracking device is axially compressed between said head and said patient to form a complete circuit, wherein said complete circuit is formed when said at least two circuit portions abut one another, and checking for a change in an emitted signal from said torsion tracking device with a checking device, wherein said emitted signal is produced by said complete circuit.

2. The method of claim 1, further comprising the steps of: checking said torsion tracking device for physical defects and loosening.

3. The method of claim 1, wherein said emitted signal is checked prior to implantation of said torsion tracking device and said screw into said patient.

4. The method of claim 1, wherein said emitted signal is checked after implantation of said torsion tracking device and said screw into said patient.

5. The method of claim 1, further comprising the steps of: irrigating said torsion tracking device and said screw with a fluid.

6. The method of claim 1, wherein said said checking device is an interrogation device.

7. The method of claim 6, further comprising the steps of: checking said interrogation device if said emitted signal is not detected.

8. The method of claim 7, further comprising the steps of: altering said desired torque when said emitted signal is not detected and said interrogation device is properly functioning.

9. The method of claim 7, further comprising the steps of: removing said torsion tracking device and said screw from said patient when said emitted signal is not detected and said interrogation device is properly functioning.

10. The method of claim 9, further comprising the steps of:
implanting a new torsion tracking device and a new screw into said patient to said desired torque,
irrigating said new torsion tracking device and said new screw with a fluid, and checking for said emitted signal from said new torsion tracking device.

11. A method for implanting a torsion tracking device in a patient comprising steps of:
providing a torsion tracking device and a screw,
wherein said torsion tracking device comprises an axially compressible encasing that surrounds a first distal plate, a second proximal plate, a spring, and at least two circuit portions, wherein said at least two circuit portions are attached to said first distal plate and said second proximal plate, wherein said torsion tracking device is secured around a shaft of said screw and distal to a head of said screw, wherein said spring is mounted around said shaft of said screw and provides an opposing axial force between said first distal plate and said second proximal plate, wherein said spring is configured to bias said first distal plate axially away from said second proximal plate, checking said torsion tracking device for physical defects, sliding the torsion tracking device onto said screw until a top face of said torsion tracking device is flush with said head of said screw, checking for a signal from said torsion tracking device via an interrogation device prior to implantation to determine if said torsion tracking device is functioning properly, implanting said torsion tracking device and said screw into a bone of said patient, tightening said screw into said bone to a desired torque such that said torsion tracking device is axially compressed between said head and said patient to form a complete circuit, wherein said complete circuit is formed when said at least two circuit portions abut one another, irrigating said torsion tracking device and said screw with saline solution, and checking for an emitted signal from said torsion tracking device via said interrogation device
after implantation to determine if said torsion tracking device is functioning properly, wherein said emitted signal is produced by said complete circuit.

12. The method of claim 11, further comprising the steps of:
checking said interrogation device if said emitted signal is not detected.

13. The method of claim 11, further comprising the steps of:
altering said desired torque when said emitted signal is not detected and said interrogation device is properly functioning.

14. The method of claim 11, further comprising the steps of:
removing said torsion tracking device and said screw from said patient when said emitted signal is not detected and said interrogation device is properly functioning.

15. The method of claim 13, further comprising the steps of:
implanting a new torsion tracking device and a new screw into said patient to said desired torque,
irrigating said new torsion tracking device and said new screw with a fluid, and
checking for said emitted signal from said new torsion tracking device.

* * * * *